United States Patent [19]

Eich

[11] Patent Number: 4,712,014
[45] Date of Patent: Dec. 8, 1987

[54] RADIATION LAMP UNIT

[76] Inventor: Helmut Eich, Uhlandstrasse 7, 7417 Reutlingen-Pfullingen, Fed. Rep. of Germany

[21] Appl. No.: 871,347

[22] Filed: Jun. 6, 1986

[30] Foreign Application Priority Data

Jun. 8, 1985 [DE] Fed. Rep. of Germany ....... 3520659

[51] Int. Cl.$^4$ .................. G21G 4/00; A61N 00/00
[52] U.S. Cl. .................. 250/494.1; 250/504 R; 128/395; 128/396
[58] Field of Search ............. 250/493.1, 494.1, 504 R; 128/362, 395, 396

[56]  References Cited
U.S. PATENT DOCUMENTS 3,062,987 11/1962 Cuffman ............................. 128/396
3,986,513 10/1976 Stull ................................. 128/395
4,558,700 12/1985 Mutzhas ............................. 128/395
4,624,259 11/1986 Welt ................................. 128/396

Primary Examiner—Bruce C. Anderson
Attorney, Agent, or Firm—Sughrue, Mion, Zinn, Macpeak and Seas

[57]   ABSTRACT

A radiation lamp unit with a housing (1), in which are fitted a number of highly-polished concave reflectors (3), with light-orange radiation lamps (4), arranged in their focal point areas, and with UV-B and UV-C lamps (9, 10) secured to bases (7, 8) of two lamp units (5, 6), arranged apart from each other and symmetrical about the center axis of the housing. A drive motor (12) provides for a limited swivel motion of the lamp units in the longitudinal direction of the housing.

7 Claims, 4 Drawing Figures

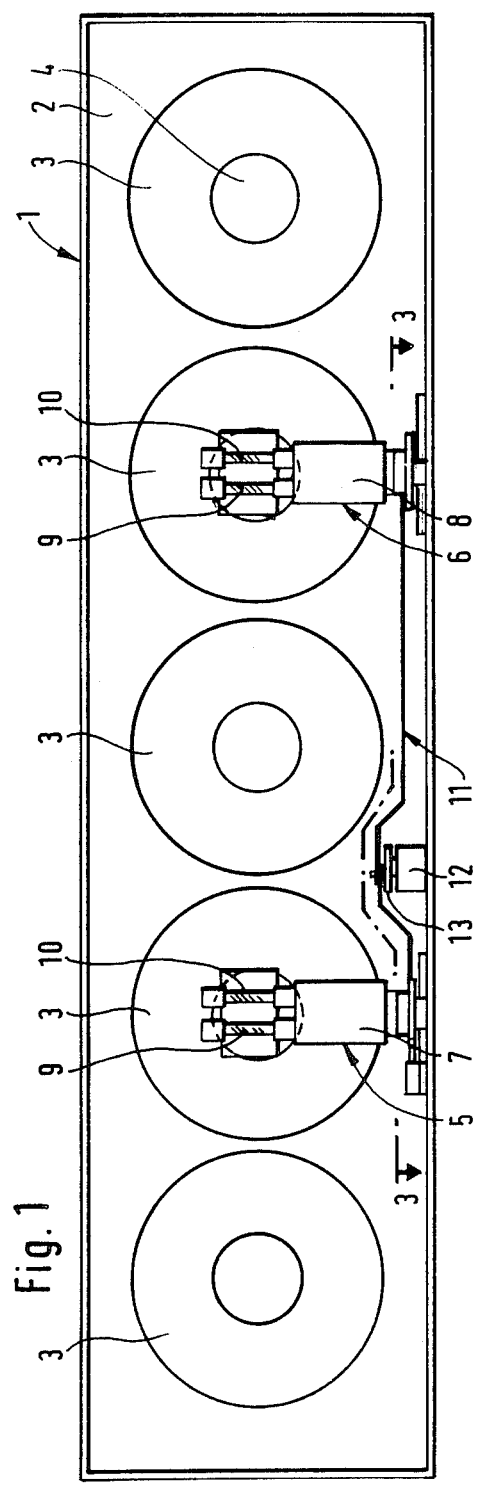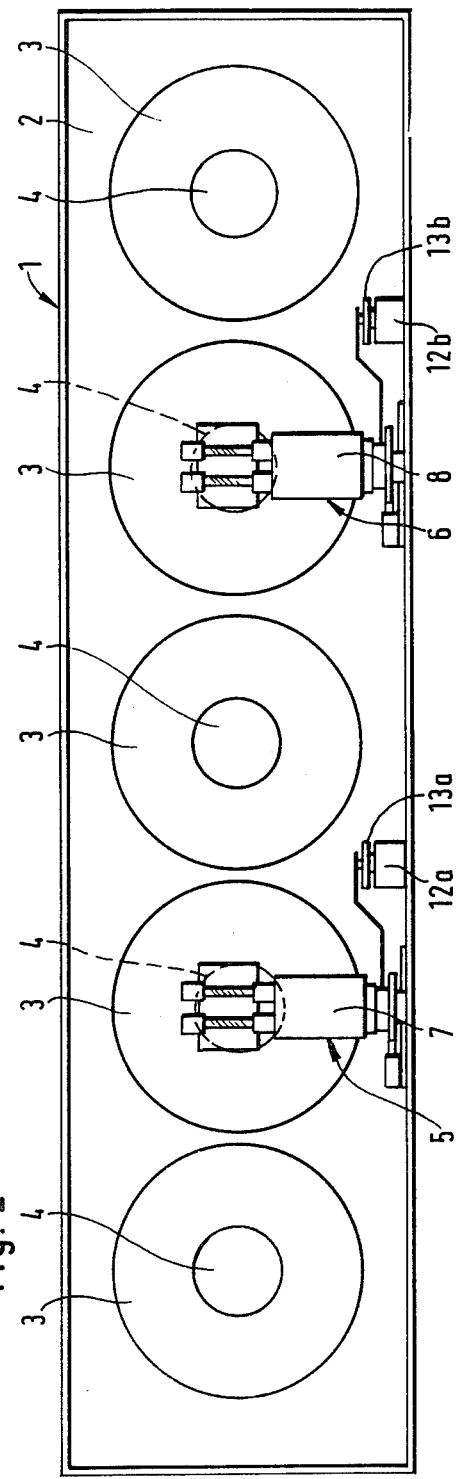

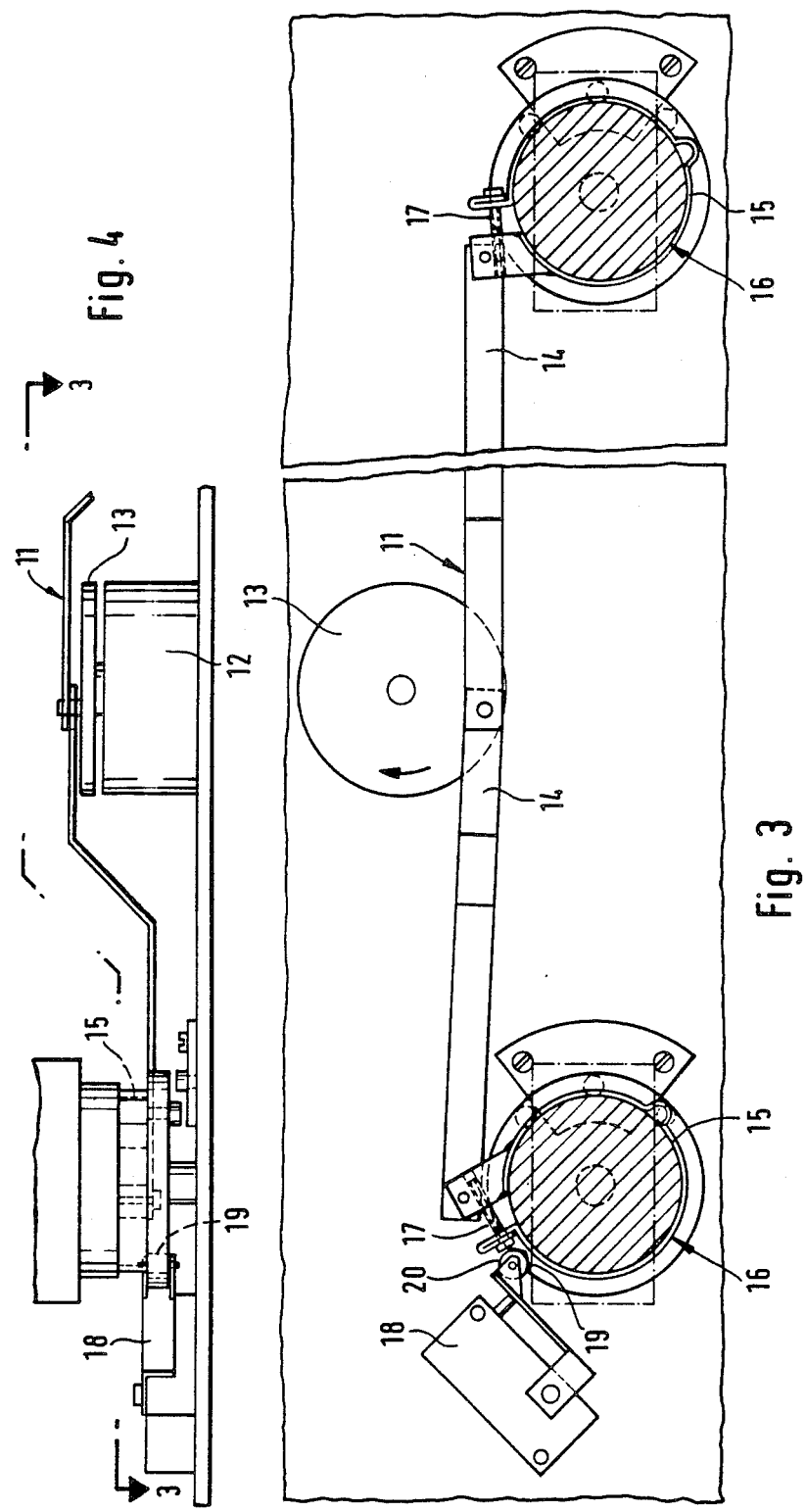

RADIATION LAMP UNIT

BACKGROUND OF THE INVENTION

The invention relates to a radiation lamp unit with a housing containing a number of highly-polished concave reflectors, with light-orange radiation lamps arranged in their focal point areas, and at least one UV lamp which is secured on a base of a lamp unit.

Such radiation lamp units, developed and constructed by the applicant, are well known.

It has been determined, however, that previously known radiation lamp units are not completely satisfactory for the treatment of a large body area, e.g. Psoriasis covering a large part of the body, simply because uniform treatment is not possible when the distance between the radiation sources and the affected parts of the body increases. It is particularly evident, even if the UV lamps are swivelled to and fro, if one UV-B and one UV-C lamp are fitted in the lamp base, since in one case one lamp is closer to the part of the body to be treated than the other.

SUMMARY OF THE INVENTION

To solve this problem, the invention uses two UV lamp units instead of one, preferrably arranged symmetrical to the center axis, and also in front of the focal point area of a light-orange radiation lamp in each case.

It may also be favorable in certain cases to arrange each of the UV lamp units between two concave reflectors.

The lamp units preferably have two UV lamps secured to a common base.

BRIEF DESCRIPTION OF THE DRAWINGS

FIG. 1 is a front view of a radiation lamp in accordance with the invention with a common drive system;

FIG. 2 is a front view of a radiation lamp with a separate drive system;

FIG. 3 is a top view of the drive system of FIG. 1,

FIG. 4 is a partial side view of the drive system.

DETAILED DESCRIPTION OF THE PREFERRED EMBODIMENTS

FIG. 1 shows a radiation lamp provided with a housing 1, as used in conjunction with a control unit (not shown here). The housing is seen from the front or patient side, but has an almost semi-circular cross-section. The individual elements of the radiation lamp are only indicated chematically as they are not important to the invention.

Concave reflectors 3 are disposed in large circular openings, covered by a screen 2. Light-orange radiation lamps are arranged at the focal point areas of the concave reflectors. The latter are highly-polished, and the openings in the screen are designed in such a way that the radiation reflected by the concave reflector surfaces can emerge unobstructed.

At the second and fourth positions designated by reference numerals 5 and 6, a UV-B and a UV-C lamp 9 and 10 are arranged on each of the bases 7 and 8. Mirrors are disposed behind the UV lamps, shielding them to the rear.

A drive system 11 is provided for these lamp positons, in this case consisting of one drive motor 12 with a drive disk 13 and drive arms 14. This drive system will be explained in more detail.

FIG. 2 shows there is an arrangement similar to that in FIG. 1, whereby the same elements are again provided with the same reference numerals. In this case two separate drive systems are provided, each with one drive motor 12a, 12b and a drive dish 13a, 13b. However, these individual systems function in the same way.

FIG. 3 shows the individual features of the FIG. 1 drive system. The drive motor 12 continuously rotates the drive disk 13. Two drive arms 14 are eccentrically coupled to the disk, and act as pushers on slip couplings 16 lying in continuous grooves 15 of the corresponding bases 7 and 8. The driving force of the slip couplings 16 can be finely adjusted using an adjusting screw 17. An end switch 18 is also provided, and is actuated by a roller 20 entering a stop groove 19.

FIG. 4 shows the drive arrangement from the side. One of the drive arms in FIGS. 3 and 4 is dispensed with when two separate drive systems in accordance with FIG. 2 are provided.

It is important that the swivel movement or pivotal reciprocation of the lamps is only 90°, i.e. 45° to both sides, seen in the longitudinal direction of the radiation lamps. The lamps in positions 5 or 6 can be manually adjusted to any position by means of the slip couplings 16. If the drive system is switched on and both lamp units are not in the same rotational position, the left drive mechanism, which can be seen in FIG. 3, remains in its end position due to the slippage of its coupling 16 until the right drive mechanism has reached the same position. From this point on, both lamp units move completely uniformly and synchronously. This mode of operation is ensured by the end switch 18, the stop groove 19, and the roller 20 entering the stop groove.

With such a construction it is possible, for example, to set one lamp unit for a certain direction and to initially leave the other lamp unit fixed, swivveling it afterwards. It is also possible to swivel both lamps alternately under program control, or to stop them in a certain position.

This new arrangement means that the application possibilities for treatment of large-area skin damage are decisively improved.

I claim:

1. A radiation lamp unit, comprising: an elongate housing (1), a plurality of highly-polished concave reflectors (3) mounted in the housing, an equal plurality of light-orange radiation lamps (4) individually disposed at focal point areas of the reflectors, and two UV lamp units (9, 10) secured to mounting bases (7, 8) spaced apart from each other and symmetrically disposed about a center axis of the housing.

2. A lamp unit in accordance with claim 1, wherein the UV lamp units are individually disposed in front of the focal point areas of light-orange radiation lamps (4), and are shielded from the latter by mirrors reflective on both sides.

3. A lamp unit in accordance with claims 1 or 2, wherein five concave reflectors (3) are provided in a row, each with a light-orange radiation lamp, and the two UV lamp units are individually arranged in front of the second and fourth reflectors.

4. A lamp unit in accordance with claim 3, wherein each UV lamp unit contains a UV-B lamp and a UV-C lamp supported by a common base (7, 8).

5. A lamp unit in accordance with claim 4, further comprising means for swivelling the base (7, 8) of each UV lamp unit through a limited angular range in a longitudinal direction of the housing.

6. A lamp unit in accordance with claim 5, wherein the swivelling means comprises:
   (a) a drive motor (12),
   (b) a drive disk (13) rotatably driven by the motor,
   (c) a continuous circular groove (15) defined in the base of each UV lamp unit,
   (d) two adjustably tensioned clamping rings (16) individually disposed in each groove, extending therearound, and defining slip couplings with associated lamp unit bases, and
   (e) a pair of drive arms (14) individually connected at their one ends to the clamping rings and eccentrically connected at their other ends to the drive disk such that, upon startup with the two UV lamp units in unequal rotational positions, one of the clamping rings will slip until equal rotational positions are established.

7. A lamp unit in accordance with claim 5, wherein the swivelling means comprises:
   (a) two drive motors (12a, 12b),
   (b) two drive disks (13a, 13b) individually rotatably driven by the motors,
   (c) a continuous circular groove (15) defined in the base of each UV lamp unit,
   (d) two adjustably tensioned clamping rings (16) individually disposed in each groove, extending therearound, and defining slip couplings with associated lamp unit bases, and
   (e) a pair of drive arms (14) individually connected at their one ends to the clamping rings and individually eccentrically connected at their other ends to the drive disks such that, upon startup with the two UV lamp units in unequal rotational positions, one of the clamping rings will slip until equal rotational positions are established.

* * * * *